United States Patent [19]

Li

[11] E Re. 29,842

[45] Reissued Nov. 21, 1978

[54] UNTRIAKONTAPEPTIDE WITH OPIATE ACTIVITY

[75] Inventor: Choh H. Li, Berkeley, Calif.

[73] Assignee: Hoffmann-La Roche Inc., Nutley, N.J.

[21] Appl. No.: 822,772

[22] Filed: Aug. 8, 1977

Related U.S. Patent Documents

Reissue of:

[64] Patent No.: 4,038,222
Issued: Jul. 26, 1977
Appl. No.: 667,747
Filed: Mar. 17, 1976

[51] Int. Cl.[2] ..... CO8L 37/00; C07C 103/52; A61K 37/00

[52] U.S. Cl. ..... 260/8; 260/112.5 R; 424/177

[58] Field of Search ..... 260/8, 112.5 R; 424/177

[56] References Cited

PUBLICATIONS

Li, et al., Biochemistry 14, pp. 947-952, 1975.
Bradbury, et al., "Proceedings of 4th Annual Amer. Peptide Sympossium, 1975".

*Primary Examiner*—Delbert R. Phillips
*Attorney, Agent, or Firm*—Samuel L. Welt; Jon S. Saxe; George M. Gould

[57] ABSTRACT

An untriakontapeptide having significant opiate agonist activity has been isolated from camel pituitary glands. The structure of this peptide has been determined and this peptide was then synthesized utilizing solid phase peptide synthesis. Both natural and synthetic material show identical physical and biological properties.

7 Claims, No Drawings

UNTRIAKONTAPEPTIDE WITH OPIATE ACTIVITY

Matter enclosed in heavy brackets [ ] appears in the original patent but forms no part of this reissue specification; matter printed in italics indicates the additions made by reissue.

BACKGROUND OF THE INVENTION

Hughes et al. Nature 258, 557 (1975), have described the isolation of a pentapeptide, H-Tyr-Gly-Gly-Phe-Met-OH- from pig brains. The pentapeptide exhibits opiate agonist activity.

This amino acid sequence occurs as residues 61 to 65 of ovine beta-lipotropin. See the papers by Li and coworkers, Nature 208, 1093 (1965); Excerpta Medica Internatl. Congr. Ser. 112, 349 (1966); and Biochem. Biophys. Res. Commun. 53, 1304 (1973).

Peptide-like substances having morphine like activity derived from bovine and porcine pituitaries have been reported by Goldstein and coworkers. Life Sciences, 16, 1775 (1975). Hughes et al. have suggested that these substances may be the peptide fragments derived from enzymatic digests of beta-lipoprotein.

DESCRIPTION OF THE INVENTION

The present invention relates to a untriakontapeptide having the following sequence:

H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-His-Lys-Lys-Gly-Gln-OH.

This material has been isolated from camel pituitary extracts and after sequencing has been synthesized utilizing classical solid phase synthesis procedures. Both the natural and synthetic peptides process significant opiate agonist activity and very low lipotropic activity.

It is of interest to note that the untriakontapeptide of the present invention has an amino acid sequence identical to the COOH-terminal 31 residues of bovine beta-lipotropin. In addition, the first five amino acid residues of the $NH_2$-terminal have the identical sequence of the Hughes et al. pentapeptide.

For purposes of convenience the untriakontapeptide of this invention shall hereafter be referred to as beta-endorphin.

The isolation of beta-endorphin from natural sources can be carried out utilizing procedures well known in the art. Preferred natural sources for this material include ovine pituitary glands, preferably camel pituitaries.

Thus, for example, whole camel pituitaries are subjected to acid acetone extraction to yield fraction D which in turn is chromatographed on a CM-cellulose column to provide component N as described by Li et al, Biochemistry 14, 947 (1975).

Purification of component N is accomplished by utilizing gel filtration and electrophoresis procedures known per se to thereby yield the desired [beta-endophine] *beta-endorphine.*

Identification of the amino acid content and sequence of beta-endorphin can be obtained by enzymatic digestion of the beta-endorphin derived from purified component N using trypsin and subtilsin digestion in a conventional manner. The digests are then mapped by paper chromatography followed by high voltage electrophoresis. After developing of the spots with ninhydrin and elution, it is found that the trypsin digestion produces 11 spots while the subtilsin digestion yields 10 spots. The spots are eluted and the amino acid content determined by an automatic analyzer while the amino acid sequence is determined by the dansyl-Edman procedure. Utilization of such procedures resulted in the determination that beta-endorphin is an untriakontapeptide having an amino acid content and sequence as set forth above.

Synthesis of beta-endorphin can be carried out employing solid phase techniques now well known in the art. In a preferred procedure amino protected glutamine, representing the —COOH terminal group of beta-endorphin, is coupled to a conventional solid phase peptide synthesis resin such as benzyhydrylamine polystyrene cross-linked with 1 to 2% divinyl benzene. The amino protecting group is then selectively removed utilizing a suitable reagent whose nature will depend on the protecting group used. In the preferred embodiment the t-butyloxycarbonyl (Boc) group is utilized for amino group protection and 50% trifluoroacetic acid in methylene chloride is the selective deprotecting agent.

After deprotection, the glutamine-resin is treated with amino protected glycine, preferably N-boc-glycine, most preferably as the preformed symmetrical anhydride of N-Boc-glycine in a manner known per se as to form a peptide bond between the free amino group of the glutamine residue and the carboxyl group of glycine.

The cycle of deprotection and coupling with the preformed symmetrical anhydrides of protected amino acids is then repeated with the remaining amino acids in the sequence order of beta-endorphin. Some of the amino acids required side-chain blocking groups besides the alpha-amino protection. Such amino acids and the blocking groups employed are as follows:

Glu(OBzl), Ser(Bzl), Lys(oBr-Z) Tyr(oBr-Z) and His(-Boc)

wherein oBr-Z is ortho bromo-benzyloxycarbonyl, Bzl is benzyl and Boc is as above.

Completion of the synthesis provided the following protected untriakontapeptide coupled to the styrenedivinylbenzene copolymer resin:

Boc-Tyr-(oBr-Z)-Gly-Gly-Phe-Met-Thr-Ser(Bzl)-Glu(OBzl)-Lys(oBr-Z)-Ser(Bzl)-Gln-Thr-Pro-Leu-Val-Thr-Leu-Phe-Lys(oBr-Z)-Asn-Ala-Ole-Ile-Lys-(oBr-Z)-Asn-Ala-His(Boc)-Lys(oBr-Z)-Lys-(oBr)-Gly-Gln- ® wherein oBr-Z, Bzl and Boc are as above and ® is the [styrene-% ] *styrene-1%* divinylbenzene copolymer.

Decoupling of the peptide from the resin is accomplished by treatment with liquid hydrogen fluoride with concomittant cleavage of all protecting group to produce the desired beta-endorphin.

In spite of the fact that beta-endorphin has the amino acid sequence of residue 61–91 of beta-lipotropin hormone the lipolytic activity of beta-endorphin is very low in comparison to the complete hormone. However, beta-endorphin has significant opiate agonist activity and this is useful as a potent, non-addictive analgesic agent. Synthetic and natural beta-endorphin have identical physical and biological properties.

A further aspect of the present invention relates to analogs of beta-endorphin which correspond to the amino acid sequence found in corresponding beta-lipotropin from porcine and human hormone. Thus in its broadest aspect the instant invention relates to untriakontapeptides of the following formula:

H-Tyr-Gly-Gly-Phe-Met-Thr-Ser-Glu-Lys-Ser-Gln-Thr-Pro-Leu-Val-Thr-Leu-Phe-Lys-Asn-Ala-Ile-X-Lys-Asn-Ala-Y-Lys-Lys-Gly-Z-OH wherein X is Ile or Val; Y is His or Tyr and Z is Gln or Glu.

The above compounds are conveniently prepared by conventional solid phase peptide synthesis in analogy to that described for beta-endorphin by substitution of the appropriate alternate amino acid in this synthesis.

The compounds of the present invention can be used as medicaments in the form of pharmaceutical preparations having direct or delayed liberation of the active ingredient which contain them in association with a compatible pharmaceutical carrier material. This carrier material can be an organic or inorganic inert carrier material suitable for enteral, percutaneous or parenteral application such as water, gelatin, gum arabic, lactose, starch, magnesium stearate, talc, vegetable oils, polyalkyleneglycols, petroleum jelly, etc. The pharmaceutical preparations can be made up in a solid form (e.g., as tablets, dragees, suppositories or capsules), in a semisolid form (e.g., as salves) or in a liquid form (e.g., as solutions, suspensions or emulsions). If necessary the pharamceutical preparations can be sterilized and/or contain adjuvant substances such as preserving, stabilizing, wetting or emulsifying agents, salts for the variation of the osmotic pressure or substances acting as buffers.

In the case of pharmaceutical preparations for systemic administration, about 5 to 750 mg/kg of a compound of the invention can be provided per administration.

The pharmaceutical preparations can be prepared in a manner known per se by mixing a compound of the invention with non-toxic solid and/or liquid carrier materials which are customary in pharmaceutical preparations and which are suitable for therapeutic administration (e.g., those carrier materials mentioned earlier) and, if desired, transforming the mixture into the desired pharmaceutical dosage form.

EXAMPLE 1

Isolation of Natural Beta-Endorphin

A total of 500 whole camel pituitary glands was extracted with acid acetone according to the procedure of Li et al. Biochemistry 14, 947 (1975) to provide fraction D. Chromatography of fraction D on a CM-cellulose column yielded 66 mg. of component N.

Gel filtration of the 66 mg. of component N on a Sephadex G-25 (fine) column in 0.1 N acetic acid. Six fractions were obtained with the following yields after lyophilization:

A-10 mg; B-7 mg; C-11 mg; D-13 mg; E-2 mg. and F-7 mg.

Fraction C was further purified by preparative electrophoresis on Whatman No. 3 MM paper in pyridine-acetic acid buffer of pH 3.7 (pyridine-HoAc-$H_2O$: 4/40/1150; v/v) for 2 hours at 400 V. The major band was eluted with 0.1 N acetic acid and lyopholized to yield 7.5 mg. of pure product. $NH_2$-terminal analysis of this material gave only tyrosine as the end group.

Amino acid analysis as carried out on a sample of the pure product according to Spackman et al., Anal. Chem. 30, 1190 (1958), utilizing an automatic analyzer. The resulting amino acid composition of this product is set forth in Table 1.

Table 1

Amino Acid Composition of Peptide Component N-Fraction C

| Amino Acid | From Acid Hydrolysates[a] | From the Sequence |
|---|---|---|
| Lysine | 5.1 | 5 |
| Histidine | 0.9 | 1 |
| Aspartic Acid | 2.0 | 2[b] |
| Threonine | 3.2 | 3 |
| Serine | 1.6 | 2 |
| Glutamic acid | 2.7 | 3[c] |
| Proline | 0.7 | 1 |
| Glycine | 3.2 | 3 |
| Alanine | 1.7 | 2 |
| Valine | 0.9 | 1 |
| Methionine | 0.6 | 1 |
| Isoleucine | 1.0[d] | 2 |
| Leucine | 2.0 | 2 |
| Tyrosine | 0.9 | 1 |
| Phenylalanine | 1.9 | 2 |

[a]Acid hydrolyses were carried out for 24 hr. at 110° with 6 M HCl.
[b]Two asparagine.
[c]Sum of one glutamic acid and two glutamine.
[d]72 hr. hydrolysis revealed the presence of two residues.

The absence of tryptophan was ascertained by color test on paper according to the procedure of Smith, Nature VII 43 (1953).

EXAMPLE 2

Structure Determination

Enzyme digestions of the product of Example 1 were performed with 1 mg. of peptide and 0.02 mg. trypsin or 0.05 mg. subtilsin in pH 8.0 buffer (0.2 M ammonium acetate) at 37° C. for 8 hours in the case of trypsin and 1 hour for subtilsin. The digests were mapped by paper chromatography (butanol/acetic acid/water: 4/1/5 (v/v)) and subsequent high voltage electrophoresis at pH 2.0 [formic acid (88%)/acetic acid/water: 218/63/719 (v/v)] for 1.5 hr. at 200 V. Maps were sprayed with 1% ninhydrin in ethanol solution and allowed to develop in the dark for 20 hours. The spots were cut out and eluted with 0.1 N ammonium hydroxide solution. The eluates were dried in the dissicator for amino acid and sequence analyses. Amino acid analysis was carried out according to Spackman et al. supra. The amino acid sequence of peptides was determined by the dansyl-Edman procedure as described by Li et al., Arch. Biochem. Biophys. 141, 705 (1970). The determination of Asp/Asn and Glu/Gln was deduced from the mobility on paper electrophoresis at pH 6.7 according to Offord, Nature 211, 591 (1966). The results are summarized in Tables 2 and 3 below.

Table 2

Amino Acid Composition[2] and Amino-terminal Residue of Trypic and Subtilisn Peptides from Component N-Fraction C

| Amino | Tryptic Peptides | | | | | | | Subtilisin Peptides | |
|---|---|---|---|---|---|---|---|---|---|
| Acid | T1 | T3 | T5 | T6 | T7 | T8 | T9 | S7 | S9 |
| Lys | 2.2 | 1.1 | 0.9 | | 1.0 | 1.0 | 1.0 | 1.1 | 1.0 |
| His | 0.9 | 1.0 | | | | | | | |
| Asp | 1.0 | 0.6 | | | 0.8 | | | 1.0 | |
| Thr | | | | | | 1.1 | 2.1 | | 1.0 |
| Ser | | | | | | 1.0 | 0.8 | | 1.1 |
| Glu | | | 1.1 | 1.0 | | 1.0 | 1.2 | | 1.8 |
| Pro | | | | | | | 0.8 | 1.1 | |
| Gly | | | 1.0 | 0.5 | | 2.0 | | | |
| Ala | 1.0 | 0.8 | | | 1.1 | | | 0.8 | |
| Val | | | | | | | 1.0 | | |

Table 2-continued

Amino Acid Composition[2] and Amino-terminal Residue of Trypic and Subtilisn Peptides from Component N-Fraction C

| Amino Acid | Tryptic Peptides | | | | | | | Subtilisin Peptides | |
|---|---|---|---|---|---|---|---|---|---|
| | T1 | T3 | T5 | T6 | T7 | T8 | T9 | S7 | S9 |
| Met | | | | | | 0.8 | | | |
| He | | | | | 2.0 | | | 2.0 | |
| Leu | | | | | | | 2.2 | | 1.0 |
| Tyr | | | | | | 0.6 | | | |
| Phe | | | | | | 1.0 | 0.9 | | |
| $NH_2$—(term.) | Asn | Asn | Lys | Gly | Asn | Tyr | Ser | Lys | Glu |

Results from 6 N HCl hydrolysates at 110° C for 24 hr. except for T7 and S7 which were hydrolyzed in 72 hr.

Table 3

Sequence Analysis on Tryptic Peptide Derivatives from Component N-Fraction C

| Peptides[a] | Sequence[b] |
|---|---|
| T8 | Tyr—Gly—Gly—Phe—Met—Thr—Ser—Glu—Lys |
| | → → → → → → → → |
| T9 | Ser—Gln—Thr—Pro—Leu—Val—Thr—Leu— |
| | → → → → → → → → |
| | —Phe—Lys |
| | → |
| T7 | Asn—Ala—Ile—Ile—Lys |
| | → → → → |
| T3 | Asn—Ala—His—Lys |
| | → → → |
| T5 | Lys—Gly—Gln |
| | → → → |
| T6 | Gly—Gln |
| | → → |

[a]See Table 2 for amino acid analysis.
[b]→, dansyl-Edman procedure

The sequence of beta-endorphin is derived from the data set forth in Table 1 of Example 1 and Tables 2 and 3 of this Example. As shown in Table 1, arginine, cystine and tryptophan are absent from component N-Fraction C. In addition, this material has only one residue each of histidine, glutamic acid, valine, methionine and tyrosine. Since the $NH_2$-terminal residue is tyrosine, tryptic peptide T8 must be located at the $NH_2$-terminus. From the amino acid and $NH_2$- terminal data of subtilsin peptide S9 (Table 2) it is apparent that T8 is linked to T9. Similarly, S7 can provide the overlap for T9 and T7.

Peptide T6 has COOH-terminal glutamine and no lysine, it may be assumed to be located at the COOH-terminus. Peptide T5 indicates the probability of Lys-Lys linkage and this is confirmed by T1 and T3 (Tables 2 and 3). Peptide T1 also serves to link T3 and T5. Thus it may be concluded that the arrangement of hyptic peptides is as follows; T8→T9→T7→T3→T5 and the complete amino acid sequence of Component N-Fraction C (beta-endorphin) is as set forth previously in the specification for the untriakontapeptide.

EXAMPLE 3

Solid Phase Synthesis of Beta-endorphin

$N^{\alpha}$-Boc-α-Benzyl-γ-Glutamyl Benzhydrylamine Resin

Attachment of α-benzyl $N^{\alpha}$-t-butoxycarbonyl glutamate to benzhydrylamine resin was performed by means of its symmetrical anhydride. A sample (2.5 g.) of benzhydrylamine hydrochloride resin containing 0.38 mmol free amine per g. was neutralized with 5% diisopropylethylamine (DIEA) in $CH_2Cl_2$ and then treated with 3 equivalents of the symmetrical anhydride in $CH_2Cl_2$ for 45 min. Five ml. of 5% DIEA in $CH_2Cl_2$ were then added followed by an additional 10 min. reaction time. The reaction was terminated by filtration and washings with three 30 ml. portions of $CH_2Cl_2$ and three 30 ml. portions of absolute ethanol. After retreatment of the resin with the same amount of symmetrical anhydride, it was dried in vacuo over $P_2O_5$ for 1 hour. Completeness of the reaction was verified by the Gisin test. After hydrolysis of a sample in propionic acid-12 N HCl, amino acid analysis gave one peak corresponding to 0.23 mmol of Gln per g. (68% cleavage). The identification of the HF cleaved product as glutamine was confirmed by thin layer chromatography in 1-butanol-acetic acid-water (4:1:1) and 1-butanol-pyridine-acetic acid-water (6:6:1.2:4.6).

Symmetrical Anhydrides of Boc-Amino Acids

The reaction of Boc-amino acids with dicyclohexylcarbodiimide was performed as follows: 1.9 mmol of Boc-amino acid in 6 ml. of methylene chloride were cooled to 0° C. and mixed with 1.6 ml. of 0.6 M N,N'-dicyclohexylcarbodiimide in methylene chloride. After stirring for 20 minutes at 0° C., the precipitate of dicyclohexylurea was removed by filtration at 25° C. and washed with 2.4 ml. of methylene chloride. The filtrate was used immediately for the coupling reaction.

Protected Beta-Endorphin Benzhydrylamine Resin

The resin just described was submitted to the following synthesis schedule: 1. Wash with three 15 ml. portions of methylene chloride (retention volume of the resin for methylene chloride was 5 ml. after filtation); (2) removal of the Boc group with 50% trifluoroacetic acid in methylene chloride for 15 min; (3) wash with two 15 ml. portions of methylene chloride; (4) wash with two 15 ml. portions of 50% dioxane in methylene chloride; (5) wash with two 15 ml. portions of methylene chloride; (6) five minutes of neutralization with 15 ml. of 5% diiosopropylethylamine in methylene chloride; (7) wash with six 15 ml. portions of methylene chloride; (8) add the solution of preformed symmetrical anhydride of Boc-amino acid and shake for 30 min; (9) add .20 equivalents of 5% diisopropylethylamine in methylene chloride and shake for another 20 min; (10) wash with three 15 ml. portions of methylene chloride; and (11) wash with three 15 ml. portions of absolute ethanol. The above cycle was repeated for the following N-protected amino acids:

Boc-Gly
Boc-Lys(oBr-Z)
Boc-Lys(oBr-Z)
Boc-His(Boc)
Boc-Ala
Boc-Asn
Boc-Lys(oBr-Z)
Boc-Ile
Boc-Ile
Boc-Ala
Boc-Asn*
Boc-Lys(oBr-Z)
Boc-Phe
Boc-Leu
Boc-Thr
Boc-Val
Boc-Leu
Boc-Pro
Boc-Thr
Boc-Gln
Boc-Ser(Bzl)
Boc-Lys(oBr-Z)
Boc-Glu(OBzl)
Boc-Ser(Bzl)

Boc-Thr
Boc-Met
Boc-Phe
Boc-Gly
Boc-Gly
Boc-Tyr(oBR-Z)

[a]After introduction of Asn, the peptide resin was dried (yield 4.7 g.) and an aliquot (400 mg.) was removed. The remainder of the peptide resin was then carried through the same schedule for incorporation of the remaining residues with two exceptions. Two treatments with 5% DIEA in methylene chloride were used for neutralization and for the second stage of anhydride couplings, trifluoroethanol was added to a concentration of 20%.

β-Endorphin

A sample (0.6 g.) of protected endorphin resin was submitted to deprotection and neutralization steps in order to remove the Boc group. The dried resin was then stirred in the presence of 1.8 ml. of anisole and 15 ml. of liquid HF at 0° C. for 1 hour. The HF was removed with a stream of nitrogen and the oily residue was washed with two 15-ml. portions of ethyl acetate. The peptide was extracted from the resin with three 15-ml. portions of 50% acetic acid and the combined filtrates were evaporated in vacuo to a small volume (3 to 5 ml.) and submitted to gel filtration on Sephadex G-10(2 × 25 cm column) in 0.5 N acetic acid. One peak (280 nm detection) was detected and lyophilization gave 110 mg. This material was then submitted to chromatography on carboxymethylcellulose. Isolation of th main peak (280 nm detection) gave 66 mg. of material. Further purification of this material was effected by partition chromatography on Sephadex G-50. Isolation of the material represented by the main peak [Folin-Lowry detection] ($R_F$ = 0.21) gave 52 mg. of highly purified beta-endorphin (19.6% yield based on the starting resin).

On thin layer chromatography (BPAW), the purified material (50 μg) gave one spot (ninhydrin detection) with an $R_F$ value of 0.35. On paper electrophoresis, synthetic beta-endorphin (50 μg samples) gave a single spot at both pH 3.7 and 6.9 with respective $R_F$ values (relative to Lys) of 0.65 and 0.42. Gel electrophoresis of the purified material (100 μg) also gave a single band at pH 4.5 for 1 hour. A sample (1 mg) was also submitted to electrofocusing in 5% polyacrylamide gel. Only one band (detection by precipitation with 12% trichloroacetic acid) was observed with an approximate pI of 10.0. Amino acid analysis after acid hydrolysis gave: $Lys_{5.2}$, $HiS_{0.9}$, $Asp_{2.2}$, $Thr_{3.0}$, $Ser_{2.1}$, $Glu_{2.1}$, $Pro_{1.1}$, $Gly_{3.0}$, $Ala_{2.1}$, $Val_{1.1}Met_{0.9}$, $Ile_{1.5}$, $Leu_{2.2}$, $Tyr_{1.0}$, and $Phe_{2.2}$. Amino acid analysis after complete enzymic digestion (first with trypsin and chymotrypsin, and then leucine amino peptidase) gave: $Lys_{3.0}$, $His_{1.0}$, $Thr_{3.2}$, $(Ser, Asn, Gln)_{3.2}$, $Glu_{1.1}$, $Pro_{0.9}$, $Gly_{3.0}$, $Ala_{2.1}$, $Val_{1.0}$, $Met_{1.2}$, $Ile_{2.0}$, $Leu_{2.1}$, $Tyr_{1.1}$ and $Phe_{1.8}$.

EXAMPLE 4

Biological Activity of Beta-Endorphin

The opiate agonist activity of natural beta-endophine was determined by the method of Simon et al., Proc. Nat. Acad. Sci. 70, 1947 (1973) using guinea pig brain membranes. The results obtained are summarized below in Table 4:

Table 4

Opiate Agonist Activity of $\beta_s$-LPH-(61 - 91) by Receptic Binding Assay

| Preparation | Dose ($10^{-7}$M) | Response[a] |
|---|---|---|
| Normophine | 0.7 | 28 ± 0.8 |
| | 7.0 | 70 ± 0.9 |

Table 4-continued

Opiate Agonist Activity of $\beta_1$-LPH-(61 - 91) by Receptic Binding Assay

| Preparation | Dose ($10^{-7}$M) | Response[a] |
|---|---|---|
| $\beta_s$-LPH-(61-91)[b] | 1.0 | 60 ± 0.7 |
| | 10.0 | 83 ± 0.2 |

[a]Percentage of inhibition of stereospecific binding. Mean ± standard error from 4 determinations.
[b]Relative potency to normorphine, 342% with a 95% confidence limit of 300 - 392 and λ = 0.044.

It is seen from the above Table that beta-endorphin has a potent opiate agonist activity; its potency being 3.42 times that for normophine on a molar basis.

The lypolytic activity of natural beta-endorphin was compared to the activity of ovine beta-lipotropin hormone in rabbit fat cells using the procedure of Li et al., Arch. Biochem. Biophys. 169, 669 (1975). The results obtained are summarized in Table 5.

Table 5

Lipolytic Activity of β-lipotropin hormone and natural β-endorphin

| Preparation | Dose | Response[a] |
|---|---|---|
| Beta-lipotropin hormone | 0.37 | 3.24 ± 0 |
| | 1.1 | 5.71 ± 19 |
| natural beta-endorphine | 1.1 | 0.66 ± 0.28 |
| | 10.0 | 1.42 ± 0.37 |
| control | 0 | 0.74 ± 0.06 |

[a]Micromole of glycerol production per gram of cells per hour. Determinations in triplicate. Values in mean ± standard error.

EXAMPLE 5

Analog of Beta-endorphin Analogous to Sequence Porcine Beta-lipotropin

The procedure of Example 3 is repeated with the exception that the first Boc-Ile amino acid is substituted with Boc-Val so as to thereby produce an analog of beta-endorphin having an amino acid sequence of the corresponding section of porcine beta-lipotropin H-Tyr-Gly-*Gly*-Phe-Met-Thr-Ser-Glu-Lys-Ser-*Gln*-Thr-Pro-Leu-Val-Thr Leu-Phe-Lys-Asn-Ala-Ile-Val-Lys Asn-Ala-His-Lys-Lys-Gly-Gln-OH

EXAMPLE 6

Analog of Beta-endorphin Analogous to Sequence Human Beta-lipotropin

The procedure of Example 3 is repeated with the exception that the carboxyl terminus group utilized is Boc-Glu(Bzl) [and], Boc-His(Boc) is replaced by Boc-Tyr(oBr-Z) *and a conventional copolystyrene-divinylbenzene resin is selected, e.g., chloromethylated copolystyrene-divinylbenzene* to thereby produce an analog of beta-endorphin having an amino acid sequence as follows:

H-Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu-OH which corresponds to that portion of the human beta-lipotropin.

I claim:

1. A compound of the formula

Boc-Tyr(oBr-Z)-Gly-Gly-Phe-Met-Thr-Ser(Bzl)-Glu(OBzl)-Lys(oBr-Z)-Ser(Bzl)-Gln-Thr-Pro-Leu-Val-Thr-Leu-Phe-Lys(oBr-Z)-Asn-Ala-Ile Ile-Lys- (oBr-Z)-Asn-Ala-His(Boc)-Lys(oBr-Z)-Lys(oBr-X)-Gly-Gln ® wherein oBr-Z is ortho bromobenzyloxycarbonyl; Bzl is benzyl; Boc is [toxycarbonyl] *t-butyloxycarbonyl and ® is styrene-divinyl-benzene copolymer resin.*

2. A compound of the formula

H-Tyr-Gly-Gly-Phe-Met-Thr-Ser-Glu-Lys-Ser-Gln-Thr-Pro-Leu-Val-Thr-Leu-Phe-Lys-Asn-Ala-Ile-X-Lys-Asn-Ala-Y-Lys-Lys-Gly-Z-OH wherein X is Ile or Val; Y is His or Tyr and Z is Gln or Glu said compound being essentially free of other biogenic peptides.

3. The compound of claim [4] *2* wherein X is Ile; Y is His and Z is Gln.

4. The compound of claim 2 wherein X is Val; Y is His and Z is Gln.

5. The compound of claim 2 wherein X is Ile; Y is Tyr and Z is Glu.

6. A compound of the formula

Boo-Tyr(oBr-Z)-Gly-Gly-Phe-Met-Thr-Ser(Bzl)-Glu(OBzl)-Lys-(oBr-Z)-Ser(BZl)-Gln-Thr-Pro-Leu-Val-Thr-Leu-Phe-Lys(oBr-Z)-Ans-Ala-Ile-Val-Lys-(oBr-Z)-Asn-Ala-His(Boc)-Lys(oBr-Z)-Lts(oBr-Z)-Glyn-Gln ® wherein OBr-Z is orthobromobenzyloxycarbonyl; Bzl is benzyl; Boc is t-butyloxcarbonyl and ® is styrene-divinylbenzene copolymer resin.

7. A compound of the formula:

Boc-Tyr(oBr-Z)-Gly-Gly-Phe-Me-Thr-Ser(Bzl)-Glu-(OBzl)-Lys-(oBr-Z)-Ser(Bzl)-Gln-Thr-Pro-Leu-Val-Thr-Leu-Phe-Lys(oBr-Z)-Asn-Ala-Ile-Ile-Lys-(oBrZ)-Asn-Ala-Tyr(oBr-Z)-Lys-(oBr-Z)-Lys(oBr-Z)-Gly-Glu(Bzl) ® wherein oBr-Z is orthobromobenzyloxycarbonyl; Bzl is benzyl; Boc is t-butyloxycarbonyl and ® is styrene-divinylbenzene copolymer resin.

* * * * *